United States Patent [19]

Holtkamp, Sr.

[11] Patent Number: Plant 7,679

[45] Date of Patent: Oct. 15, 1991

[54] AFRICAN VIOLET PLANT NAMED CANDY

[76] Inventor: Reinhold Holtkamp, Sr.,
Blumenstrasse 28, D 4242
Rees-Haffen, Fed. Rep. of Germany

[21] Appl. No.: 565,321

[22] Filed: Aug. 10, 1990

[51] Int. Cl.[5] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner

[57] ABSTRACT

A new and distinct cultivar of African violet named Candy characterized by its single pink flowers with slightly wavy, white edges; strong, upright flower stems that curve slightly toward the center to form a compact bouquet above the leaves; medium green, oval leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Candy.

The new cultivar was referred to during the breeding and selection process by the designation 247 rosa si. and is a product of a planned breeding program. The new cultivar was originated from a cross made by me in the controlled breeding program in Haffen, Federal Republic of Germany. The female, or seed parent was a cultivar designated 3 III. The male, or pollen parent was a cultivar designated 79/2/8.

Candy was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Candy has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Candy, which in combination distinguish this African violet as a new and distinct cultivar:

(1) Strong, upright flower stems curving slightly toward the center.

(2) Violet-shaped pink flowers with slightly wavy, white edges.

(3) Each plant carries 7–9 and more upright flower stems each of which carries 10–14 and more flowers.

(4) Long lasting, non-dropping flowers.

(5) Vigorous and compact grower.

(6) Plant saleable 10 to 11 weeks after potting.

(7) Seed capsules push slightly through.

(8) Medium green, oval leaves.

(9) After maturity the flowers dry off, and remain on the peduncle without becoming infected by botrytis:

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Candy.

Parentage:
- *Male parent.*—3 III.
- *Female parent.*—79/2/8.

Propagation: The new cultivar holds its distinguishing characteristics through successive propagations by leaf cuttings.

Plant: From 8 cm to 11 cm tall when grown in pots, and approximately 23–27 cm in diameter when fully grown.

Leaves:
- *General form.*—Oval.
- *Diameter.*—65–70 mm wide and 70–80 mm long.
- *Texture.*—Leatherlike.
- *Aspect.*—Hairy, slightly shiny.
- *Veins.*—Upperside: well visible; underside: well pronounced, light green, sometimes purplish red touch, shiny.
- *Color (upperside).*—Yellow-Green Group 147 A.
- *Color (underside).*—Greyed-Purple Group 186 between B and C with touches of Greyed-Green Group 194 D.
- *Petiole.*—Strong upright, purplish brown, hairy.

Flowers:
- *Buds.*—Bell-shaped, 7–9 mm just before opening, pinkish green.
- *Sepals.*—Five (5). Color: Purplish brown.
- *Calyx.*—Shape: Funnel-shaped. Aspect: Spear-shaped, hairy.
- *Peduncle.*—Character: Strong upright, hairy. Color: Purplish brown.

Individual flowers:
- *Size.*—37–42 mm.
- *Shape.*—Single violet-shaped with slightly wavy edges.

*Color* (*upperside*).—Purple Group 78 D, darker parts are Red-Purple Group 74 C to D. White edges. Under cooler temperatures and more intensive lighting, the pink tends to intensify.

*Color* (*underside*).—Purple Group 75 B to C.

*Borne.*—Each flower stem carries 10–14 and more flowers on strong, upright peduncles that are free standing above the leaves, thereby forming a compact bouquet.

*Flowering habit.*—Flowers 10–11 weeks after potting.

Reproductive organs:

*Stamens.*—Two (2). Anthers: 2 composed of 4 anther cells, seed capsule pushes slightly through.

*Filaments.*—Yellowish green with pink touch, 3–4 mm long.

*Pollen color.*—Yellow Group 7 A.

*Styles.*—6–7 mm long, pink, base of ovary light green and hairy.

Roots: Normally developed, white when young, turning slightly brownish when older.

Disease resistance: Up to date, Candy has shown very good resistance to all major violet diseases.

General observations: Candy is very attractive due to its pink flowers with white edges. A tight bouquet of flowers free standing above the leaves develops after approximately 10–11 weeks. Each of the 8–10 and more strong flower stems carries 10–14 and more single violet-shaped flowers with slightly wavy edges. The flowers are long-lasting and non-dropping and the seed capsules push slightly through. Candy is a vigorous and compact grower with medium green, oval leaves.

I claim:

1. A new and distinct cultivar of African violet named Candy, as described and illustrated, and particularly characterized by its single pink flowers with slightly wavy, white edges; strong, upright flower stems that curve slightly toward the center to form a compact bouquet above the leaves; medium green, oval leaves; profuse flowering, vigorous and compact growth habit, flowering 10–11 weeks after potting, and its long lasting and non-dropping flowers.

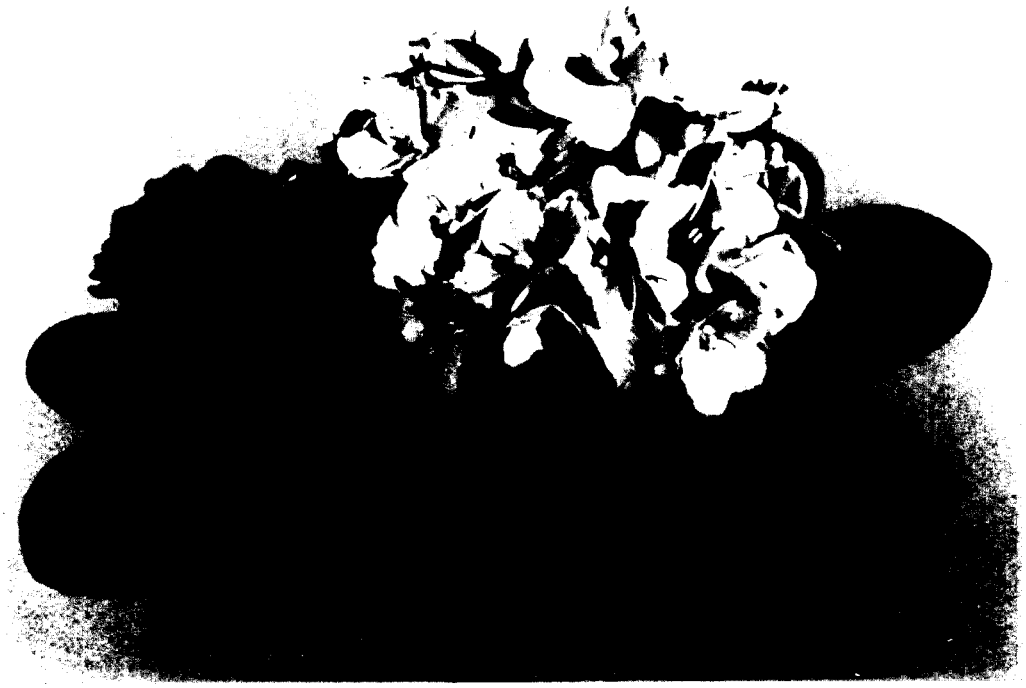

* * * * *